United States Patent
Imamoto et al.

(10) Patent No.: US 6,194,593 B1
(45) Date of Patent: Feb. 27, 2001

(54) 1, 2-BIS(DIALKYLPHOSPHINO) BENZENE DERIVATES HAVING OPTICAL ACTIVITES, PROCESS FOR PRODUCING SAME, AND RHODIUM METAL COMPLEXES CONTAINING SAME AS LIGANDS

(75) Inventors: Tsuneo Imamoto; Tomoya Miura; Hironari Yamada, all of Chiba (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 0 days.

(21) Appl. No.: 09/494,119

(22) Filed: Jan. 28, 2000

(51) Int. Cl.[7] ................ C07F 15/00; C07F 9/53
(52) U.S. Cl. ............ 556/136; 568/17; 502/166
(58) Field of Search ............... 568/17; 556/136; 502/162, 166

(56) References Cited

PUBLICATIONS

Tetrahedron Letters, by Miura et al 40(26) pp4833–4836, Jun. 1999.*

\* cited by examiner

Primary Examiner—Jean F. Vollano
(74) Attorney, Agent, or Firm—Armstrong, Westerman, Hattori, McLeland & Naughton

(57) ABSTRACT

An optically active 1,2-bis(dialkylphosphino) benzene derivative represented by the general formula (1) which is suitable as a ligand for a transition metal catalyst in asymmetrical hydrogenation is provided. Also provided is a process for producing such a benzene derivative, and a rhodium metal complex having such a benzene derivative as a ligand which is useful as an asymmetric catalyst for use in asymmetrical hydrogenation.

(I)

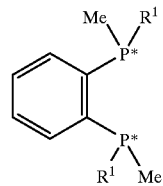

(where $R^1$ denotes a straight or branched alkyl group having 2–6 carbon atoms, and each of the asterisks denotes an asymmetric phosphorus atom).

4 Claims, No Drawings

1, 2-BIS(DIALKYLPHOSPHINO) BENZENE DERIVATES HAVING OPTICAL ACTIVITES, PROCESS FOR PRODUCING SAME, AND RHODIUM METAL COMPLEXES CONTAINING SAME AS LIGANDS

BACKGROUND OF THE INVENTION

This invention relates to a 1,2-bis(dialkylphosphino) benzene derivative having an optical activity which is suitably useful as a ligand for an asymmetric catalyst for use in asymmetrical hydrogenation, and also to a process for producing such a benzene derivative. Further, the invention relates to a rhodium metal complex containing, as a ligand, such an optically active 1,2-bis-(dialkylphosphino) benzene derivative which is suitable as an asymmetric catalyst for use in asymmetrical hydrogenation.

The development of new chiral phosphine ligands has given a great impetus to studies on asymmetric syntheses using metal catalysts so that these studies have become rapidly progressive over the last 30 years. Most of these ligands are configured so as to have a center of asymmetry on a carbon skeleton, a phosphorus atom bonded to that skeleton and two aryl groups situated on this atom. Meanwhile, little has been studied regarding P-chiral phosphine ligands structured to have dialkyl and trialkyl groups attached thereto. This is due to the fact that the latter ligands are difficult to synthesize.

Recently, the present inventors have proposed a 1,2-bis-(akylmethylphosphino) ethane having a P-chiral trialkyl group and represented by the following general formula (3):

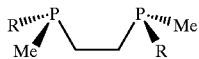
(3)

(where R denotes a cyclopentyl, cyclohexyl, tert-butyl, 1,1-diethylpropyl group or 1-adamantile) (J. Am. Chem. Soc., 120, 1635–1636, 1998). The ethane compound noted here permits a variety of α, β-unsaturated α-amino acids and their esters to be asymmetrically hydrogenated with high efficiency.

Nevertheless there still remains a demand for the development of other phosphine ligands which are optically active and particularly suitable as a ligand for use in an asymmetric catalyst in asymmetrical hydrogenation.

Accordingly, principal objects of the present invention are to provide a 1,2-bis(dialkylphosphino) benzene derivative possessing an optical activity and which is suitably useful as a ligand for an asymmetric catalyst in asymmetrical hydrogenation, a process for producing such a benzene derivative, and a rhodium metal complex containing, as a ligand, such a benzene derivative which is applicable as an asymmetric catalyst in asymmetrical hydrogenation.

SUMMARY OF THE INVENTION

As a result of the present inventors' intensive research conducted with the foregoing situation in mind, the present invention has been completed. More specifically, the invention provides a 1,2-bis(dialkylphosphino) benzene derivative having an optical activity represented by the following general formula (1):

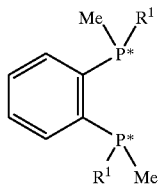
(I)

(where $R^1$ denotes a straight or branched alkyl group having 2–6 carbon atoms, and each of the asterisks denotes an asymmetric phosphorus atom).

The invention also provides a process for the production of the above-specified 1,2-bis(dialkylphosphino) benzene derivative having an optical activity, which comprises: optically resolving a 1,2-bis(dialkylphosphinoyl) benzene compound by the use of benzoyl tartrate in optically active form, the benzene compound being represented by the following general formula (2):

(2)

(where $R^1$ is the same as defined above); and subsequently reducing the benzene compound, thus made optically active, with a reducing agent.

In addition, the invention provides a rhodium metal complex containing as a ligand the 1,2-bis (dialkylphosphino) benzene derivative having an optical activity represented by the above general formula (1).

DETAILED DESCRIPTION OF THE INVENTION

The substituting group $R^1$ in the formula (1) expressing the 1,2-bis(dialkylphosphino) benzene derivative of the present invention denotes a straight or branched alkyl group having 2–6 carbon atoms. Specific examples of the alkyl group include ethyl, isopropyl, n-propyl, isobutyl, n-butyl, sec-butyl, tert-butyl, isoheptyl, n-heptyl, isohexyl, n-hexyl, cyclopentyl, cyclohexyl and like groups.

The 1,2-bis(dialkyl-phosphino) benzene derivative of the formula (1) is exemplified by (R,R)-1,2-bis (ethylmethylphosphino) benzene, (S,S)-1,2-bis-(ethylmethylphosphino) benzene, (R,R)-1,2-bis(iso-propylmethyl-phosphino) benzene, (S,S)-1,2-bis(isopropyl-methyl-phosphino) benzene, (R,R)-1,2-bis(n-propylmethylphosphino)-benzene, (S,S)-1,2-bis(n-propylmethylphosphino) benzene, (R,R)-1,2-bis-(isobutylmethylphosphino) benzene, (S,S)-1,2-bis(isobutyl-methyl-phosphino) benzene, (R,R)-1,2-bis(n-butylmethyl-phosphino) benzene, (S,S)-1,2-bis(n-butylmethylphosphino) benzene, (R,R)-1,2-bis(sec-butylmethylphosphino) benzene, (S,S)-1,2-bis(sec-butylmethyl-phosphino) benzene, (R,R)-1,2-bis(tert-butylmethyl-phosphino) benzene, (S,S)-1,2-bis(tert-butylmethylphosphino) benzene, (R,R)-1,2-bis-isoheptylmethyl-phosphino) benzene, (S,S)-1,2-bis (isoheptylmethyl-phosphino) benzene, (R,R)-1,2-bis(n- heptylmethylphosphino) benzene, (S,S)-1,2-bis(n-heptylmethyl-phosphino) benzene, (R,R)-1,2-bis-(isohexylmethylphosphino) benzene, (S,S)-1,2-bis (isohexyl-methyl-phosphino) benzene, (R,R)-1,2-bis(n-hexylmethyl-phosphino) benzene, (S,S)-1,2-bis(n-hexylmethylphosphino) benzene, (R,R)-1,2-bis(cyclopentylmethyl-phosphino) benzene, (S,S)-1,2-bis (cyclopentylmethyl-phosphino) benzene, (R,R)-1,2-bis (cyclohexylmethylphosphino) benzene, (S,S)-1,2-bis(cyclohexylmethylphosphino) benzene and the like.

The process of the present invention is described below.

According to the invention, the process for the production of the 1,2-bis(dialkylphosphino) benzene derivative of an optically active nature expressed by the formula (1) is constituted, for example, by a first step in which a 1,2-bis-(dialkylphosphinoyl) benzene compound of the formula (2) is subjected to optical resolution in the presence of optically active benzoyl tartrate so as to prepare a 1,2-bis(dialkylphosphinoyl) benzene of an optically active nature, and a second step in which the 1,2-bis-(dialkyl-phosphinoyl) benzene, thus made optically active, is then reduced with a reducing agent, thereby yielding the desired compound, i.e., the 1,2-bis(dialkyl-phosphino) benzene derivative expressed by the formula (1).

(First Step)

In the first step, the substituting group $R^1$ in the formula (2) expressing the 1,2-bis(dialkylphosphinoyl) benzene for use as a starting material is equivalent to the substituting group $R^1$ in the formula (1) expressing the desired compound, namely the 1,2-bis(dialkylphosphino) benzene derivative. The 1,2-bis- dialkyl-phosphinoyl) benzene of the formula (2) may be prepared in a conventional manner. For example, the starting material is easily obtainable in accordance with the following reaction formula (I):

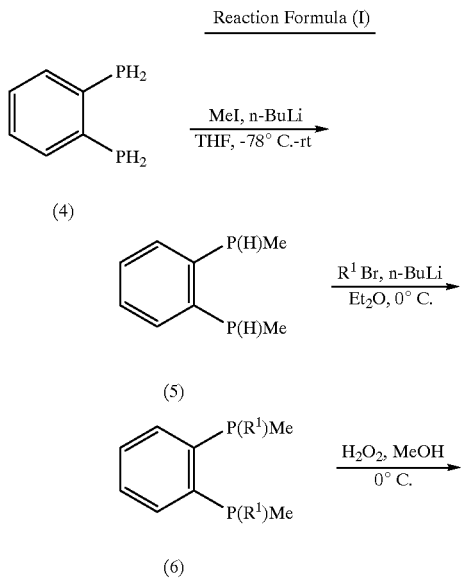

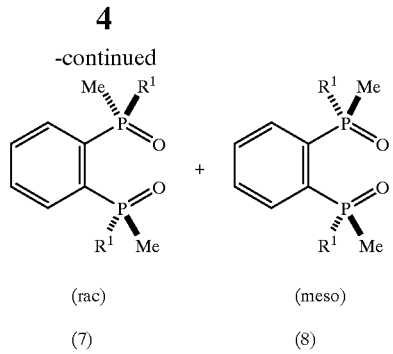

Reaction Formula (I)
(where $R^1$ is the same as defined above).

To be more specific, 1,2-bis(phosphino) benzene (the compound (4) in the above reaction formula) is methylated at a temperature of −78° C. to room temperature and with use of solvents such as n-butyllithium and methyl iodide so as to prepare 1,2-bis(methyl-phosphino) benzene (the compound (5)). Into a reactor are thereafter introduced the compound (5), ethyl ether and n-butyl-lithium, and reaction is carried out with gradual dropping of an alkyl bromide for several hours at a temperature of −10 to 0° C. to thereby obtain a 1,2-bis(alkylmethylphosphino) benzene (of the formula (6) in the above reaction formula). Next, the compound of the formula (6) is dissolved in methanol, followed by reaction with hydrogen peroxide for several hours at a temperature of 0° C. to provide a 1,2-bis-(alkylmethylphosphinoyl) benzene in racemic arrangement, that is, as a combination of a rac form of the formula (7) and a meso form of the formula (8). For convenience, the formulas (7) and (8) are consolidated herein as the general formula (2).

In order to effect optical resolution of the 1,2-bis(dialkylphosphinoyl) benzene of the formula (2), benzoyl tartrate in optically active form is used as a resolving agent. Here, both a (−) form and a (+) form of benzoyl tartrate are acceptable. The amount of the benzoyl tartrate to be used is usually in the range of 0.5–1.2 times per mol, preferably approximately 1.0 time per mol of the 1,2-bis(dialkylphosphinoyl) benzene of the formula (2).

A solvent is used for optical resolution and is not restricted insofar as it is capable of dissolving the 1,2-bis-(dialkylphos-phinoyl) benzene of the formula (2) and the benzoyl tartrate, is inert with both of these compounds and also able to separate a diastereoisomeric salt. The solvent may be exemplified by alcohols such as methanol, ethanol, n-propanol and the like, ketone type solvents such as acetone, methyl isobutyl ketone and the like, ester type solvents such as ethyl acetate and the like, ether type solvents such as methyl butyl ether, dioxane, diethyl ether and the like, aromatic type solvents such as toluene, xylene, chlorobenzene and the like, nitrile type solvents such as acetonitrile and the like, and combinations thereof. These solvents may contain water.

To perform the first step, a 1,2-bis(dialkylphosphinoyl) benzene of the formula (2) and benzoyl tartrate of a selected optical activity are dissolved in a given type of solvent, whereby a slightly soluble diastereoisomeric salt is separated. In the case where a (−)—dibenzoyl tartrate is used as a resolving agent, a (−)-(S,S)-1,2-bis(dialkylphosphinoyl) benzene and a slightly soluble diastereoisomeric salt are formed and separated. On the other hand, the use of a (+)—dibenzoyl tartrate for resolution purposes forms and separates a (+)-(R,R)- 1,2-bis(dialkylphos-phinoyl) benzene and a slightly soluble diastereoisomeric salt.

The temperature at which a slightly soluble diastereo isomeric salt is separated is from the freezing to boiling points of the solvent used and is usually in the range of from 0 to 100° C. The slightly soluble diastereoisomeric salt, in crystalline form, is easily separable from the reaction system by means of a conventional solid-liquid separation method such as filtration, centrifugation and the like. The resultant diastereo isomeric salt is decomposed by acidic or alkaline treatment in an aqueous solvent or in a hydrophobic-aqueous solvent so that a (−)-(S,S)-1,2-bis(dialkylphosphinoyl) benzene or a (+)-(R,R)-1,2-bis-(dialkylphosphinoyl) benzene is provided. Such a benzene compound may be recrystallized, if desired, to enhance the purity.

(Second Step)

In the second step, the above-specified (−)-(S,S)-1,2-bis (dialkylphosphinoyl) benzene or (+)-(R,R)-1,2-bis(dialkylphosphinoyl) benzene is reacted with a suitable reducing agent to yield a desired optically active 1,2-bis (dialkylphosphino) benzene derivative expressed by the formula (1). In this instance, the (+)-(R,R)-1,2-bis(dialkylphosphinoyl) benzene is reduced to provide an (S,S) form, whereas the (−)-(S,S)-1,2-bis(dialkyl-phosphinoyl) benzene is reduced to provide an (R,R) form.

The reducing agent eligible for the present invention is generally a silane compound, but is not limited thereto. The silane compound includes trichlorosilane, dichlorosilane, methyl dichlorosilane, dimethyl chlorosilane, phenyl dichlorosilane, phenyl methyl chlorosilane, diphenyl chlorosilane, phenylsilane and the like. Of these compounds, phenylsilane is preferred.

The amount of the reducing agent to be used is usually in the range of 5–10 times per mol of the 1,2-bis(phos-phinoyl) benzene. The reaction temperature is usually in the range of from 105 to 110° C., and the reaction time is in the range of 3–24 hours, preferably 4–10 hours. Thus, 1,2-bis-(dialkylphosphino) benzene derivative of the formula (1) can be obtained with high optical purity while being held asymmetricly without racemization.

The 1,2-bis(dialkylphosphino) benzene derivative expressed by the general formula (1) and provided in accordance with the present invention can cooperate with a transition metal in forming a complex when used as a ligand. The complex-forming transition metal may be exemplified by rhodium, ruthenium, iridium, palladium, nickel and the like, of which rhodium is preferred. In the formation of a complex from a rhodium metal by the use, as a ligand, of the 1,2-bis(dialkyl-phosphino) benzene derivative of the formula (1), an acceptable method is available which is disclosed in, for example, "Experimental Chemistry Series" (4th edition, edited by the Japanese Chemical Society and published by Maruzen Co., volume 18, pages 327–353). For example, a rhodium metal complex can be derived from a reaction of the 1,2-bis(di-alkylphosphino) benzene derivative of an optically active nature according to the present invention and bis(cyclooctane-1,5-diene) rhodium tetrafluoro-borate.

Specific examples of the rhodium complex to be attained by the present invention may be chosen from Rh((S,S)-(1)) Cl, Rh((S,S)-(1))Br, Rh((S,S)-(1))I, [Rh((S,S)-(1)) (cod)] $BF_4$, [Rh((S,S)-(1)) (cod)]$ClO_4$, [Rh((S,S)-(1)) (cod)]$PF_6$, [Rh((S,S)-(1)) (cod)]$BPh_4$, [Rh((S,S)-(1)) (nbd)]$BF_4$, [Rh ((S,S)-(1)) (nbd)]$ClO_4$, [Rh((S,S)-(1)) (nbd)]$PF_6$, [Rh((S,S)-(1)) (nbd)]$BPh_4$, Rh((R,R)-(1))Cl, Rh((R,R)-(1))Br, Rh((R,R)-(1))I, [Rh((R,R)-(1)) (cod)]$BF_4$, [Rh((R,R)-(1)) (cod)]$ClO_4$, [Rh((R,R)-(1)) (cod)]$PF_6$, [Rh((R,R)-(1)) (cod)]$BPh_4$, [Rh((R,R)-(1)) (nbd)]$BF_4$, [Rh((R,R)-(1)) (nbd)]$ClO_4$, [Rh ((R,R)-(1)) (nbd)]$PF_6$, [Rh((R,R)-(1)) (nbd)]$BPh_4$ and the like. In the present invention, [Rh((S,S)-(1)) (cod)]$BPh_4$ is preferred among these rhodium complexes. In the above nomenclatures, the FIG. "(1)" denotes a 1,2-bis (dialkylphosphino) benzene derivative of the formula (1), the term "cod" denotes 1,5-cyclooctadiene, the term "nbd" denotes norbornadiene, and the term "Ph" denotes phenyl.

EXAMPLES

The present invention will be described hereinbelow in greater detail by way of examples. These examples should be construed as illustrative, but not as restrictive.

Reference Example (Synthesis of (R,R)-1,2-bis(isopropylmethylphosphinoyl) benzene for use as a starting material in a first step)

Into a reactor were charged 10.5 g (61.7 mmol) of 1,2-bis-(methylphosphino) benzene, 82.23 ml (120.5 mmol) of n-butyllithium and 30 ml of ethyl ether, and reaction was carried out with gradual dropping of 11.7 ml (125 mmol) of bromopropane at −10° C. for 2 hours. Thereafter, the reaction mixture was treated in a known fashion to isolate a desired product, namely 1,2-bis(isopropyl-methylphosphino) benzene (in an amount of 12.4 g and in a yield of 79%), by distillation (at a boiling point of 110° C./0.4 mmHg).

Subsequently, 85 g (46.6 mmol) of the 1,2-bis(isopropylmethylphosphino) benzene thus obtained was mixed with 24 ml (200 mmol) of a 30% concentration of aqueous hydrogen peroxide and 30 ml of methanol. Reaction was carried out at 0° C. for 1 hour to prepare 13.3 g of 1,2-bis (isopropylmethylphosphino) benzene as a combination of a rac form and a meso form. When the resultant benzene compound was then recrystallized in an ethyl acetate solvent, a racemic form of 1,2-bis(isopropylmethylphosphino) benzene was obtained in an amount of 1.5 g (equal to a yield of 11%).

Example 1

(First Step)

The racemic form of 1,2-bis(isopropylmethylphosphino) benzene obtained above in the reference example was mixed in an amount of 1.5 g (5.24 mmol) with 1.97 g (5.24 mmol) of a (+) form of dibenzoyl tartrate and 35 ml of ethyl acetate. Thus, a slightly soluble diastereoisomeric salt was separated and collected. The salt so obtained was crystallized in ethyl acetate and then incorporated with 1 M of NaOH, whereby an (R,R)-1,2-bis(isopropyl-methylphosphinoyl) benzene was provided in an amount of 543 mg (with an optical purity of 99% and a yield of 35%). The resultant benzene compound was identified by the following data.

melting point: 209–210° C.

$[\alpha]^{27}_D$ +10.2 (c 1.00, $CHCl_3$)

$^1$H NMR (400 MHz, $CDCl_3$, δ): 0.96 (dd, $J_{HP}$=16.6, 7.3 Hz, 6H), 1.33 (dd, $J_{HP}$=16.6, 7.1 Hz, 6H), 1.87 (d, $J_{HP}$=12.9 Hz, 6H), 2.64–2.80 (m, 2H), 7.59–7.65 (m, 2H), 8.04 (br, s, 2H)

$^{13}$C NMR (100 MHZ, $CDCl_3$, δ): 15.1 (d, $J_{CP}$=5.0 Hz), 16.3 (d, $J_{CP}$=68.6 Hz), 28.9 (d, $J_{CP}$=72.0 Hz), 130.7, 130.8 133.6

$^{31}$P NMR (160 MHz, $CDCl_3$, δ): 48.0

IR (KBr): 2970, 2880, 1300, 1190, 1170, 1120, 890

FAB MS: 287: ($M^+$+H, 100)

Elementary Analysis found: C: 58.78%, H: 8.44% calculated: as $C_{14}H_{24}O_2P_2$, C: 58.73%, H: 8.45%

X-ray Analysis orthorhomic space group 2₁2₁2₁, a=11.509 (5), Å, b=16.319 (3), Å, c=8.505 (2), Å, v=1597.4 (7), Å³, z=4, $d_{calc}$=1.190 g cm⁻³, F (000)=616, μ (Mo, Kα=2.66 cm⁻¹, λ (Mo, Kα=0.71070, Å, 2555 reflection measured, 244 observed (I>3.00 σ(1)), 163 variable, R=0.034, Rw=0.050, GOF 1.11 measured, 244 observed (I>3.00 σ(1)), I26 variable, R=0.0880, Rw=0.107, GOF 2.23

Flack parameter=0.089 (10)

(Synthesis of (R,R)-1,2-bis(isopropylmethylphosphino) benzene in a second step)

Into a reactor were introduced 94.5 mg (0.33 mmol) of the (R,R)-1,2-bis(isopropylmethylphosphinoyl) benzene obtained in the first step and 0.5 ml (5.26 mmol) of phenylsilane as a reducing agent. Reaction was performed for 6 hours at 110° C. to prepare 91.5 mg of an (S,S)-1,2-bis (isopropylmethylphosphino) benzene (with an optical purity of 97%).

Example 2

(Synthesis of a rhodium metal complex)

200 Mg (0.75 mmol) of the (S,S)-1,2-bis (isopropylmethyl-phosphino) benzene obtained in Example 1 was reacted with 304 mg (0.75 mmol) of [Rh (cod)₂] BF₄ for 1 hour at −20° C. The reaction product was recrystallized with tetrahydrofuran (at −20 to −10° C.) so that a rhodium metal complex was obtained. X-ray analysis confirmed that the resulting complex contained, as a ligand, the (S,S)-1,2-bis(isopropylmethylphosphino) benzene derivative. This was identified by the following data.

$C_{22}H_{36}BF_4P_2Rh$: molecular weight 552.18 orthorhomic space group C222₁, a=13.35 (1), Å, b=16.84 (1), Å, c=10.975 (3), Å, v=2467 (2), Å, z=4, $d_{calc}$=1.486 g cm⁻³, F(000)=1136, μ (Mo, Kα)=8.57 cm⁻¹, λ (Mo, Kα)= 0.71070, Å, 1159 reflection measured, 1157 observed (I>1.00 σ(I)), I 26 variable, R=0.0880, Rw=0.107, GOF 2.23

(Evaluation of a rhodium metal complex used as a catalyst in asymmetrical hydrogenation)

Performance evaluation was made with regard to the catalytic activity of the rhodium complex of (S,S)-1,2-bis-(isopropylmethyl-phosphino) benzene obtained in Example 2 when used as a catalyst in asymmetrically hydrogenating a methyl ester of dehydroamino Reaction Formula (II)

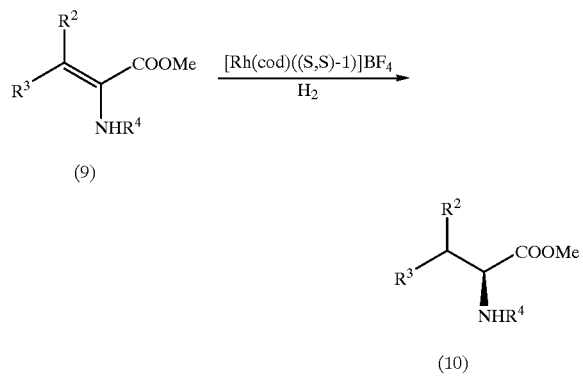

Reaction Formula (II)

The substituting groups R², R³ and R⁴ in the above reaction formula are indicated in Table 1 in which R² and R³ of each of Nos. 6 and 7 mean that they have formed, together with their respective bonding carbon atoms, a saturated single ring having a carbon atom number of 6 or 5. The catalyst was added in an amount of 0.2% by mol based on the weight of an α-amino acid methyl ester expressed by the formula (9). The reaction system was pressurized with hydrogen gas, followed by reaction at 0° C. for 20–180 minutes. The optical purities of the test compounds expressed by the formula (10) were measured and the results are tabulated in Table 1. The an optical purities were determined by means of quantitative analysis and with use of HPLC (Daicel Chiralcel OJ, OD-H) or GC (Chromapack's Chriral-L-Val Column). In order to decide the absolute configuration of the test compound, the sequences of elution associated with HPLC or GC were compared to certain reference values (J. Am. Chem. Soc., 120, 1635, 1998).

TABLE 1

| No | R² | R³ | R⁴ | Optical purity (absolute configuration) |
|----|-----|-----|-----|-----|
| 1 | Hydrogen atom | Hydrogen atom | acetyl group | 97% (S) |
| 2 | Hydrogen atom | phenyl group | acetyl group | 97% (S) |
| 3 | Hydrogen atom | phenyl group | benzoyl group | 96% (S) |
| 4 | Hydrogen atom | 3-MeO—4-AcOC₆H₃ | acetyl group | 98% (S) |
| 5 | Methyl group | Methyl group | acetyl group | 87% (S) |
| 6 | | —(CH₂)₅— | acetyl group | 89% (S) |
| 7 | | —(CH₂)₄— | acetyl group | 77% (S) |

The present invention provides a novel 1,2-bis(dialkyl-phosphino) benzene derivative of an optically active nature which is suitable as a ligand for a transition metal catalyst in asymmetrical hydrogenation. A rhodium metal complex having such a benzene derivative as a ligand exhibits significant advantages as as asymmetric catalyst for use in asymmetrical hydrogenation.

What is claimed is:

1. A 1,2-bis(dialkylphosphino) benzene having an optical activity, characterized in that the 1,2-bis dialkylphosphino) benzene is represented by the following formula (1):

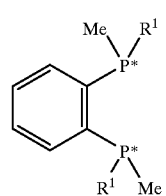

(1)

(wherein R¹ denotes a straight or branched alkyl group having 2–6 carbon atoms, and each of the asterisks denotes an asymmetric phosphorus atom).

2. A process for producing a 1,2-bis(dialkylphosphino) benzene having an optical activity as set forth in claim 1, characterized in that the process comprises: optically resolving a 1,2-bis(dialkylphosphinoyl) benzene compound represented by the formula (2):

(2)

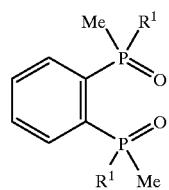

(wherein $R^1$ is the same as defined in claim 1) by using optically active benzoyl tartrate; and subsequently reducing the benzene compound thus made with a reducing agent.

3. A process for producing 1,2-bis(dialkylphosphino) benzene having an optical activity according to claim 2, wherein the reducing agent is phenylsilane.

4. A rodium metal complex characterized in that the complex contains, as a ligand, the 1,2-bis(dialkylphosphino) benzene having an optical activity as set forth in claim 1.

\* \* \* \* \*